United States Patent
Guruswamy et al.

(10) Patent No.: US 9,421,270 B2
(45) Date of Patent: Aug. 23, 2016

(54) SURFACTANT-COPOLYMER COMPLEXES USEFUL FOR SUSTAINED DRUG RELEASE

(71) Applicant: Council of Scientific and Industrial Research, New Delhi (IN)

(72) Inventors: Kumaraswamy Guruswamy, Maharashtra (IN); Venugopal Edakkal, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/406,037

(22) PCT Filed: Jun. 7, 2013

(86) PCT No.: PCT/IN2013/000360
§ 371 (c)(1),
(2) Date: Dec. 5, 2014

(87) PCT Pub. No.: WO2013/183068
PCT Pub. Date: Dec. 12, 2013

(65) Prior Publication Data
US 2015/0174251 A1  Jun. 25, 2015

(30) Foreign Application Priority Data
Jun. 7, 2012 (IN) .................. 1754/DEL/2012

(51) Int. Cl.
*A61K 47/32* (2006.01)
*A61K 31/045* (2006.01)
*A61K 47/26* (2006.01)
*A61K 47/10* (2006.01)
(Continued)

(52) U.S. Cl.
CPC . *A61K 47/32* (2013.01); *A61K 8/11* (2013.01); *A61K 8/8164* (2013.01); *A61K 8/86* (2013.01); *A61K 9/006* (2013.01); *A61K 31/045* (2013.01); *A61K 47/10* (2013.01); *A61K 47/26* (2013.01); *A61Q 11/00* (2013.01); *A61Q 19/00* (2013.01); *A61K 2800/10* (2013.01); *A61K 2800/56* (2013.01); *A61K 2800/652* (2013.01)

(58) Field of Classification Search
CPC .......... A61K 2800/10; A61K 2800/56; A61K 2800/652; A61K 31/045; A61K 47/10; A61K 47/26; A61K 47/32; A61K 8/11; A61K 8/8164; A61K 8/86; A61K 9/006; A61Q 11/00; A61Q 19/00
See application file for complete search history.

(56) References Cited

U.S. PATENT DOCUMENTS 5,690,911 A   11/1997   Mirajkar et al.
6,221,399 B1   4/2001   Rolfes et al.

OTHER PUBLICATIONS

Jones, D. S. et al. (2003). Rheological and mucoadhesive characterization of polymeric systems composed of Poly(methylvinylether-co-maleic anhydride) and Poly(vinylpyrrolidone), designed as platforms for topical drug delivery. Journal of Pharmaceutical Sciences, 92(5), 995-1007.

(Continued)

*Primary Examiner* — Aradhana Sasan
(74) *Attorney, Agent, or Firm* — John P. White; Cooper & Dunham LLP

(57) ABSTRACT

The invention discloses a surfactant-copolymer complex for delivery of hydrophobic compounds in sustained release; wherein the surfactant is a non-ionic surfactant; and copolymer is poly (maleic acid-alt-vinyl methyl ether). The present invention also provides a process for preparation of the surfactant-copolymer complex.

10 Claims, 7 Drawing Sheets

(51) Int. Cl.
- *A61K 8/81* (2006.01)
- *A61K 8/86* (2006.01)
- *A61Q 19/00* (2006.01)
- *A61Q 11/00* (2006.01)
- *A61K 9/00* (2006.01)
- *A61K 8/11* (2006.01)

(56) References Cited

OTHER PUBLICATIONS

Puspendu, D. and Somasundaran, P. (2005). Interactions of hydrophobically modified polyelectrolytes with nonionic surfactants. Langmuir, 21(9), 3950-3956.

Notification of Transmittal of the International Search Report and the Written Opinion of the International Searching Authority, or the Declaration, including an International Search Report [re-issued version] and Written Opinion of the International Searching Authority, mailed Mar. 21, 2014 by the European Patent Office in connection with PCT International Application No. PCT/IN2013/000360, filed Jun. 7, 2013.

Notification Concerning Transmittal of International Preliminary Report on Patentability (Chapter I of the Patent Cooperation Treaty), including an International Preliminary Report on Patentability and Written Opinion of the International Searching Authority, mailed Dec. 18, 2014 by the International Bureau of WIPO in connection with PCT International Application No. PCT/IN2013/000360, filed Jun. 7, 2013.

SURFACTANT-COPOLYMER COMPLEXES USEFUL FOR SUSTAINED DRUG RELEASE

CROSS-REFERENCE TO RELATED APPLICATIONS

This application is a §371 national stage of PCT International Application No. PCT/IN2013/000360, filed Jun. 7, 2013, claiming priority of Indian Patent Application No. 1754/DEL/2012, filed Jun. 7, 2012, the contents of each of which are hereby incorporated by reference in their entirety.

FIELD OF INVENTION

The present invention relates to a surfactant-copolymer complex for sustained delivery of hydrophobic compounds such as antibacterials, ointments, drugs, bioactives, perfumes, flavors, pesticides etc. More particularly, the present invention relates to surfactant-copolymer complexes which are composed of a nonionic surfactant and a copolymer, poly(maleic acid-alt-vinyl methyl ether) useful as delivery devices that are capable of spatial localization. Further, the present invention also relates to a process for the preparation of surfactant-copolymer complex.

BACKGROUND AND PRIOR ART OF THE INVENTION

Large number of methods for compound delivery in a variety of applications such as personal care, health & agricultural applications etc. has been reported. Specifically, in oral care applications, materials that are targeted at teeth enamel, gums, etc. in the oral cavity are often sub optimally used as they get washed out during use. Therefore, materials that are able to carry a payload of antibacterials, active compounds, etc. and that can specifically target areas in the oral cavity or in general the area of application and deliver the payload over a period of time are of great use.

The use of such delivery methods can significantly bring down the amount of antibacterial, active compounds, etc., which are used in current formulations as the desired or even better effects may be achieved in lower amount of required active compound which would be localized and be released over a sustained period of time. This would bring down the costs of the formulations especially in oral care products, where the quantum of the active compound is deliberately kept high considering the sub-optimal use. Further, by continuous delivery of an optimal dose, dangers associated with abrupt release of a high loading of the antibacterial compound are eliminated. The inhibiting costs of such compounds may also call for new methods of delivery.

To achieve these purposes, Polyelectrolyte-surfactant complexes (PSC's) may be one of the many options. PSCs are unique materials with the ability to spontaneously self-assemble into highly ordered nanostructures. PSCs are typically formed by the complex formation of polyelectrolytes and/or oppositely charged ionic surfactants, usually in aqueous solution. Macromolecules with hydrophobic groups as side chains have important applications in many industries and medicine, such as in drug delivery because of their unique associative behavior and special rheological properties. In addition, these polymers can serve as simplified models of natural polyelectrolytes. The interactions of surfactant and hydrophobically modified polymers are considered to be the result of complexes formed between surfactant and polymer due to electrostatic and hydrophobic forces. The presence of intramolecular micelles allows the solubilization of compounds with normally low water solubility. The solubilized compounds can have sizable effects on both intra- and intermolecular interactions. Extensive work has been done in the area to optimize the polymer surfactant complexes for their maximum utilization.

Strauss et. al. in J. Polym. Sci. 1951, 6, 649 have employed the hydrolyzed form of the regularly alternating copolymers of maleic anhydride and alkyl vinyl ethers because of their aggregation behavior in solution. U.S. Ser. No. 10/512,228 discloses a surfactant comprising a triblock copolymer including a hydrophilic block, a charged water-soluble block and a hydrophobic block for gene therapy applications.

U.S. Ser. No. 11/998,981 discloses that, by including a suitable polymer-micelle complex in a spin dope, one can electrospin fibers to include materials that may not otherwise be capable of being electrospun into fibers, either in a particular solvent or in any solvent.

U.S. Pat. No. 5,690,911 discloses an aqueous oral composition comprising an effective amount of halogenated diphenyl ether or phenolic antibacterial compound such as triclosan, a mixture of an anionic surfactant and non-ionic surfactants at a weight ratio of about 14:1 to about 9:1, and anionic polymeric polycarboxylate such as methyl vinyl ether/maleic anhydride copolymer, in an orally acceptable vehicle containing less than 60% by weight water. Further, the anionic surfactant is sodium lauryl sulfate; and the nonionic-surfactant is selected from polyoxyethylenesorbital fatty ester, polyethoxylated glycerol, alkyl glucoside.

Deo et. al in Langmuir 2005, 21, 3950-3956 discloses the study of the interactions of a nonionic surfactant such as penta-ethylene glycol mono n-dodecyl ether ($C_{12}EO_5$), with a hydrophobically modified anionic polymer i.e. poly(maleic acid/octyl vinyl ether) (PMAOVE), in aqueous solutions by involving measurements of surface tension, viscosity, electron paramagnetic resonance (EPR), light scattering, and fluorescence.

US2012087962 discloses a personal care article comprising absorbent, cellulosic substrate impregnated with an impregnation formulation having activity to de-activate pathogenic micro-organisms; the coating comprises an acidic polymer such as Gantrez™ S-96 and Gantrez™ S-97; a surfactant and an organic carboxylic acid such as citric acid. Further, the surfactant comprises an anionic surfactant or non-ionic surfactant selected from the Tween™ such as Tween 20™ or Polysorbate™ family Polysorbate 20™.

The effectiveness of the antibacterial, drugs or bioactive compounds contained in the materials employed in personal care products or oral care products is dependent upon the delivery of antibacterial or bioactive compounds at the areas of application.

According to the reported methods, the materials employed in oral care applications that are targeted at teeth enamel, gums, etc. in the oral cavity are often suboptimally used and they get washed out during its use. Therefore, such materials carrying or containing antibacterials, drug or bioactive compounds do not effectively deliver the antibacterials, drug or bioactive compounds specifically at the areas of the application which leads to the use of excessive amounts of active compounds in the preparation of oral care products or personal care products.

Therefore, there is need in the art to provide a material which would be able to carry a payload of antibacterials, drugs or bioactive compounds and specifically target the areas in the oral cavity, and also would feasibly deliver the antibacterial, drug or bioactive compounds at the area of application in an efficient manner.

To overcome the aforesaid limitations, the present discloses a surfactant-copolymer complex for delivery of hydrophobic compounds such as antibacterials, ointments, drugs, bioactives, perfumes, flavors, pesticides etc., with controlled release; and a viable process for the preparation thereof. Specifically, the present invention shows how careful formulation can be used to create a novel structure comprising of hydrophobic compound-loaded non-ionic micellar structures that complex with a copolymer. The copolymer enables targeting of the complex to specific areas, while the structure of the complex allows for controllable and sustained release of the hydrophobic compound.

OBJECTS OF THE INVENTION

Main object of the present invention is to provide a surfactant-copolymer complex which is used as delivery devices for compounds such as antimicrobials, ointments, drugs, bioactives, perfumes, flavors, pesticides etc.

Another object of the present invention is to provide a surfactant-copolymer complex for delivery of hydrophobic compounds in sustained release.

Yet another object of the present invention is to provide a process for the preparation surfactant-copolymer complex

SUMMARY OF THE INVENTION

Accordingly, present invention provides a hydrophobic compound loaded surfactant-copolymer complex for delivery of the hydrophobic compounds in sustained release comprising hydrophobic compound in the range of 0.1% to 10% (by weight), surfactant in the range of 0.1 to 30% (by weight) and copolymer in the range of 0.1% to 30% (by weight) remaining being a solvent. The present invention provides also a process for the preparation of hydrophobic compound loaded surfactant-copolymer complex comprising the steps of: (a) dispersing copolymer in solvent in the ratio ranging between 1% to 40% to obtain turbid solution of copolymer; (b) dissolving the hydrophobic compound in surfactant in the ratio ranging between 1% to 50% (weight of hydrophobic compound by weight of the surfactant) at temperature in the range of 10° C. to 80° C. to obtain hydrophobic compound-surfactant water to obtain surfactant solution loaded with hydrophobic compound; (d) adding surfactant solution loaded with hydrophobic compound as obtained in step (c) to the turbid solution of copolymer as obtained in step (a) to afford hydrophobic compound loaded surfactant-copolymer complex.

ABBREVIATIONS $C_{12}E_9$: nonaoxyethylene-n-dodecyl ether
PMAVME: poly(maleic acid-alt-vinyl methyl ether)
SAXS: Small angle X-ray scattering pattern
PEI: polyethylene imine
SDS: Sodium dodecyl sulfate

DETAILED DESCRIPTION OF THE INVENTION

Figure 1:
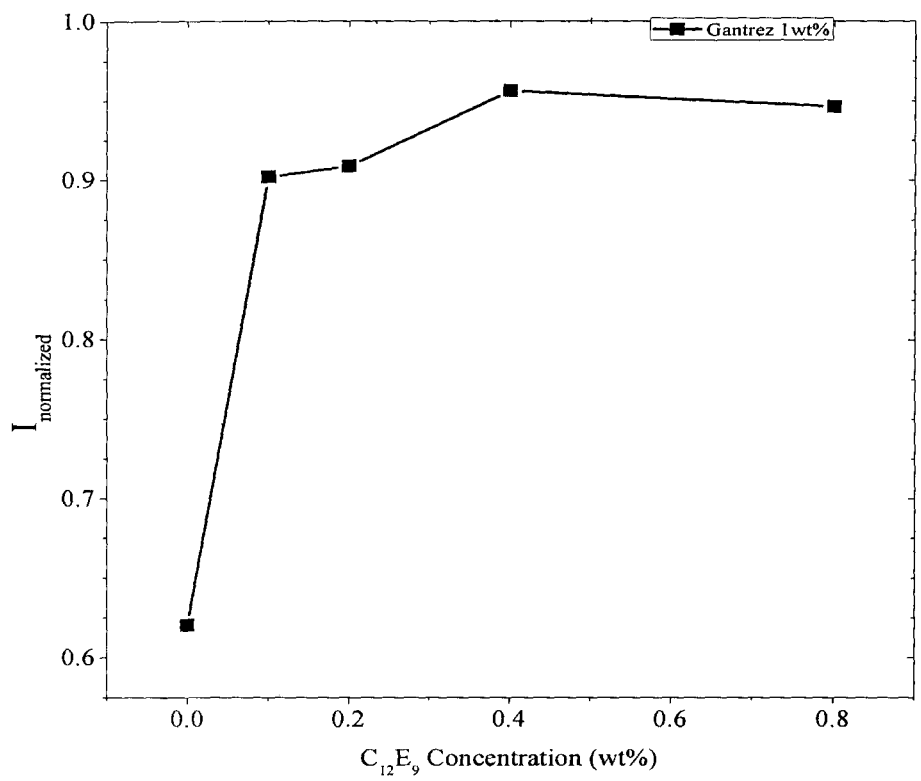
FIG. 1 depicts transmitted intensity for a 1% dispersion of copolymer, as a function of surfactant concentration.

While the invention is susceptible to various modifications and alternative forms, specific aspect thereof has been shown by way of examples and graphs and will be described in detail below. It should be understood, however that it is not intended to limit the invention to the particular forms disclosed, but on the contrary, the invention is to cover all modifications, equivalents, and alternative falling within the spirit and the scope of the invention as defined by the appended claims.

The Applicants would like to mention that the examples are mentioned to show only those specific details that are pertinent to understanding the aspects of the present invention so as not to obscure the disclosure with details that will be readily apparent to those of ordinary skill in the art having benefit of the description herein.

The terms "comprises", "comprising", or any other variations thereof, are intended to cover a non-exclusive inclusion, such that a process, polymer composition, complex composition that comprises a list of components does not include only those components but may include other components not expressly listed or inherent to such process, polymer composition, complex composition. In other words, one or more elements in a system or process proceeded by "comprises . . . a" does not, without more constraints, preclude the existence of other elements or additional elements in the system or process.

In the following detailed description of the aspects of the invention, reference is made to the accompanying graphs that form part hereof and in which are shown by way of illustration specific aspects in which the invention may be practiced. The aspects are described in sufficient details to enable those skilled in the art to practice the invention, and it is to be understood that other aspects may be utilized and that changes may be made without departing from the scope of the present invention.

In accordance with the above aspects, the invention will now be described in detail in connection with certain preferred and optional embodiments, so that various aspects thereof may be more fully understood and appreciated.

Accordingly, the present invention relates to a hydrophobic compound loaded surfactant-copolymer complex for sustained release of hydrophobic compounds comprising hydrophobic compound in the range of 0.1% to 10% (by weight), surfactant in the range of 0.1 to 30% (by weight) and copolymer in the range of 0.1% to 30% (by weight) and remaining being a solvent.

In other embodiment of the present invention, the hydrophobic compound is selected from the group consisting of antibacterials, ointments, drugs, bioactives, perfumes, flavors, pesticides and combination thereof.

In other embodiment of the present invention, the surfactant used is a nonionic surfactant.

In yet another embodiment of the present invention, the nonionic surfactant is selected from the group consisting of nonaoxyethylene-n-dodecyl ether ($C_{12}E_9$), polysorbate 20 (Tween 20), polysorbate 40 (Tween 40), polysorbate 60 (Tween 60), polysorbate 80 (Tween 80) or combination thereof.

In yet another embodiment of the present invention, the copolymer is poly (maleic acid-alt-vinyl methyl ether).

In yet another embodiment of the present invention, the copolymer poly (maleic acid-alt vinyl methyl ether) is not limited to copolymer of methyl vinyl ether and maleic acid but also includes its anhydride, alkali or alkaline salts, C1 to C6 alkyl esters, free acids or like thereof.

In yet another embodiment of the present invention, the weight ratio of surfactant to copolymer is 1:1.

In yet another embodiment of the present invention, the hydrophobic compound is in the range of 1 to 50% by weight of the surfactant-copolymer complex.

In yet another embodiment of the present invention, the solvent is selected from the group consisting of distilled deionized water, glycerine, ethanol or combination thereof In other aspect of the present invention, a process for the preparation of hydrophobic compound loaded surfactant-copolymer complex comprising the steps of:
  a) dispersing copolymer in solvent in a ratio ranging between 1% to 40% to obtain turbid solution of copolymer;
  b) dissolving the hydrophobic compound in surfactant in a ratio ranging between 1% to 50% (weight of hydrophobic compound by weight of the surfactant) at temperature in the range of 10° C. to 80° C. to obtain hydrophobic compound-surfactant mixture;
  c) adding hydrophobic compound-surfactant mixture as obtained in step (b) in water to obtain surfactant solution loaded with hydrophobic compound;
  d) adding surfactant solution loaded with hydrophobic compound as obtained in step (c) to the turbid solution of copolymer as obtained in step (a) to obtain hydrophobic compound loaded surfactant-copolymer complex.

In yet another embodiment of the present invention, the surfactant is nonionic surfactant selected from the group consisting, of nonaoxyethylene-n-dodecyl ether ($C_{12}E_9$), polysorbate 20 (Tween 20), polysorbate 40 (Tween 40), polysorbate 60 (Tween 60), and polysorbate 80 (Tween 80) or combination thereof.

In yet another embodiment of the present invention, the copolymer is poly (maleic acid-alt vinyl methyl ether).

In yet another embodiment of the present invention, the poly (maleic acid-alt vinyl methyl ether) used is not limited to copolymer of methyl vinyl ether and maleic acid but also includes its anhydride, alkali or alkaline salts, C1 to C6 alkyl esters, free acids or like thereof.

In yet another embodiment of the present invention, solvent used is selected from the group consisting of distilled deionized water, glycerine, ethanol or combination thereof.

The present invention provides a surfactant-copolymer complex for the delivery of hydrophobic compounds in sustained release; wherein the surfactant is a nonionic surfactant and copolymer is poly (maleic acid-alt vinyl methyl ether).

According to the invention, a surfactant, preferably nonionic surfactant forms a micellar structure in water that can be loaded with hydrophobic compounds such as antibacterials, ointments, drugs, bioactives, perfumes, flavors, pesticides etc. These hydrophobic compound loaded nonionic surfactant micelles complex with poly (maleic acid-alt-vinyl methyl ether) [i.e. PMAVME], a commercial alternating copolymer called Gantrez. Such surfactant-copolymer complex is exhibited to be stable in aqueous and anionic mediums by associating the nonionic surfactant micelles with PMAVME copolymers. These surfactant-copolymer complexes provide targeting of the hydrophobic compound to the area of application and enable better release and controlled delivery of the hydrophobic compounds to the areas of applications.

The nonionic surfactant is selected from the group consisting of nonaoxyethylene-n-dodecyl ether ($C_{12}E_9$), polysorbate 20 (Tween 20), polysorbate 40 (Tween 40), polysorbate 60 (Tween 60) and polysorbate 80 (Tween 80). Gantrez polymer is not limited to copolymer of methyl vinyl ether and maleic acid but also includes its anhydride, alkali or alkaline salts, C1 to C6 alkyl esters, free acids and like thereof. Gantrez is approved for use in oral care formulations as it adheres to the oral cavity and prevents gum disease. The maleic acid groups of poly (maleic acid-alt-vinyl methyl ether) dissociate in water to form anionic carboxyl functionalities.

Inventors have harnessed the adhesive ability of the Gantrez copolymer and associated the surfactant micelles with the Gantrez copolymers, so that the Gantrez copolymer carries surfactant micelles as a "cargo". These surfactant-Gantrez complexes are structurally represented as pearls on a string, wherein the pearls are the surfactant micelles loaded with threads these and specifically anchors them to the oral cavity.

The invention provides a process for preparation of a surfactant-copolymer complex for delivery of hydrophobic compounds in sustained release comprising of;
  a) dispersing the copolymer in a mixture of distilled deionized water and alcohol or glycerol to obtain a turbid solution of copolymer; and
  b) adding a hydrophobic compound loaded surfactant micellar solution to the turbid solution of copolymer as obtained in step a) to afford a clear solution of surfactant-copolymer complex, loaded with the hydrophobic compound.

Accordingly, the surfactant is selected from a group of nonionic surfactant such as nonaoxyethylene-n-dodecyl ether (i.e. $C_{12}E_9$), polysorbate 20 (Tween 20), polysorbate 40 (Tween 40), polysorbate 60 (Tween 60), polysorbate 80 (Tween 80); and the copolymer is selected from poly (maleic acid-alt vinyl methyl ether)[i.e. PMAVME]. The PMAVME copolymer is dispersed readily in water to obtain a turbid (i.e. milky) solution of PMAVME copolymer. The vinyl methyl ether group of PMAVME copolymer is rendered with enough hydrophobicity to prevent complete "molecular dissolution". When a nonionic surfactant is added to the turbid (i.e. milky) dispersion of PMAVME copolymer, a decrease in turbidity is observed and a clear solution of nonionic surfactant-PMAVME complex is obtained. Further, the clear solution is obtained for 1:1 copolymer and nonionic surfactant. (FIG. 1). The data in the remainder of this specification relates to the 1:1 complex, viz. the complex of 1 part of the PMAVME copolymer with 1 part of the nonionic surfactant.

The surfactant-copolymer (i.e. nonionic surfactant-PMAVME) complex is composed of surfactant micellar structures into which hydrophobic compounds are loaded, on a hydrophobic/anionic alternating copolymer of PMAVME that specifically adheres to areas of application. Such surfactant-copolymer complexes have better release and controlled delivery. Various studies were carried out for the determination of structure and characteristics of surfactant-copolymer complex such as specific viscosity, static light scattering study, small angle X-ray scattering study, release profile study, activity study etc.

According to invention, the structure and characteristics of the surfactant-copolymer complex so formed were studied as per the following parameters.

Specific Viscosity Study

Figure 2:
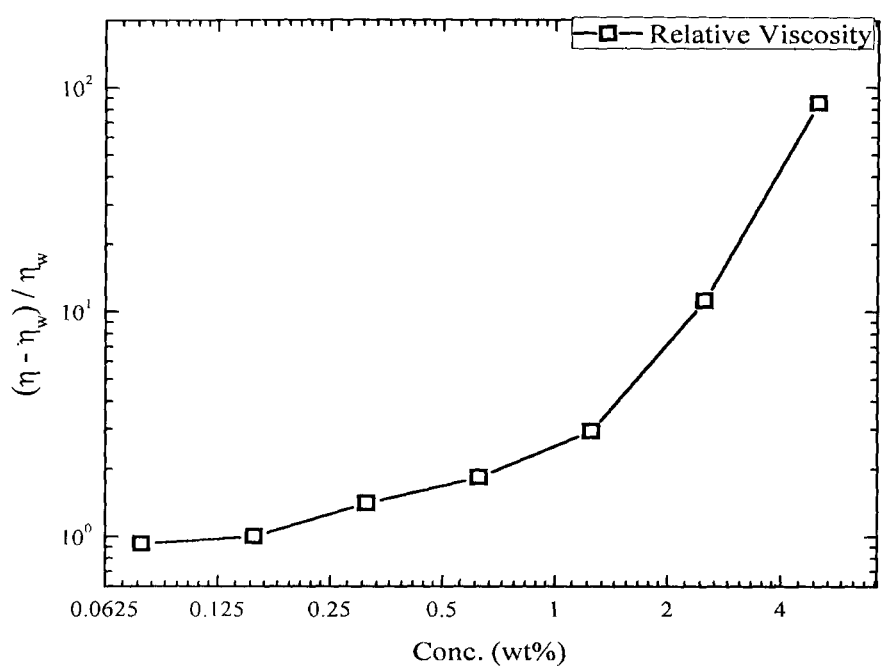
FIG. 2 depicts specific viscosity as a function of PMAVME:$C_{12}E_9$ (1:1) concentration in water.

The specific viscosity study of the $C_{12}E_9$-PMAVME complex was performed; and the specific viscosity of $C_{12}E_9$-PMAVME complex in 1:1 molar ratio is detected to be approximately 1, even at low concentrations (0.0625%). The specific viscosity study revealed that the $C_{12}E_9$-PMAVME complex was in an unentangled, overlapped state even at the low concentrations, due to the charge on the PMAVME copolymer. At concentrations near 4%, the specific viscosity increases to about 100, indicating the onset of entanglements, FIG. 2. Therefore, the complex behaves, essentially, like a linear polyelectrolyte.

Static Light Scattering Pattern Study

Figure 3:
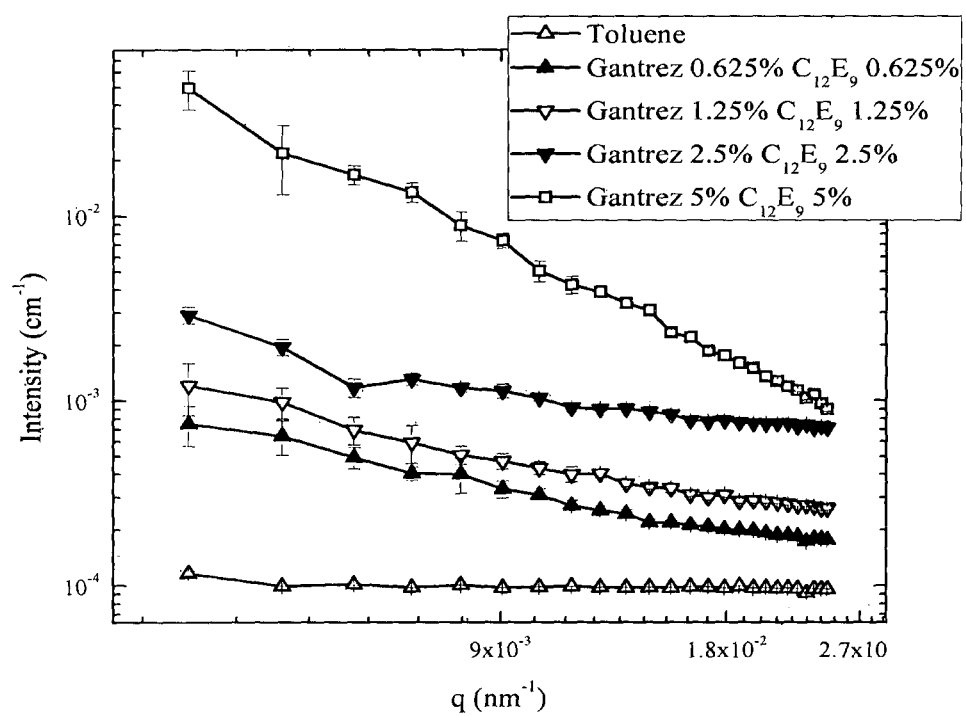
FIG. 3 depicts absolute intensity as a function of PMAVME:$C_{12}E_9$ (1:1) concentration, obtained by subtracting the water scattering intensity from that of the complex, and scaling by the appropriate Rayleigh ratio for a toluene standard.

Static light scattering from the $C_{12}E_9$-PMAVME samples in 1:1 molar ratio as a function of concentration reveals a qualitative change in the q-dependence with increase in concentration as depicted in FIG. 3. A pronounced q-dependence ($I \sim q^{-2}$) for a concentration of 5% (compare with $\sim q^0$ for 0.625%) over a q range of 0.003 $nm^{-1}$ to 0.02 $nm^{-1}$ was observed; which indicates concentration fluctuations at length scales of microns, and was consistent with the turbidity data.

Small Angle X-Ray Scattering (SAXS) Pattern Study

Figure 4:
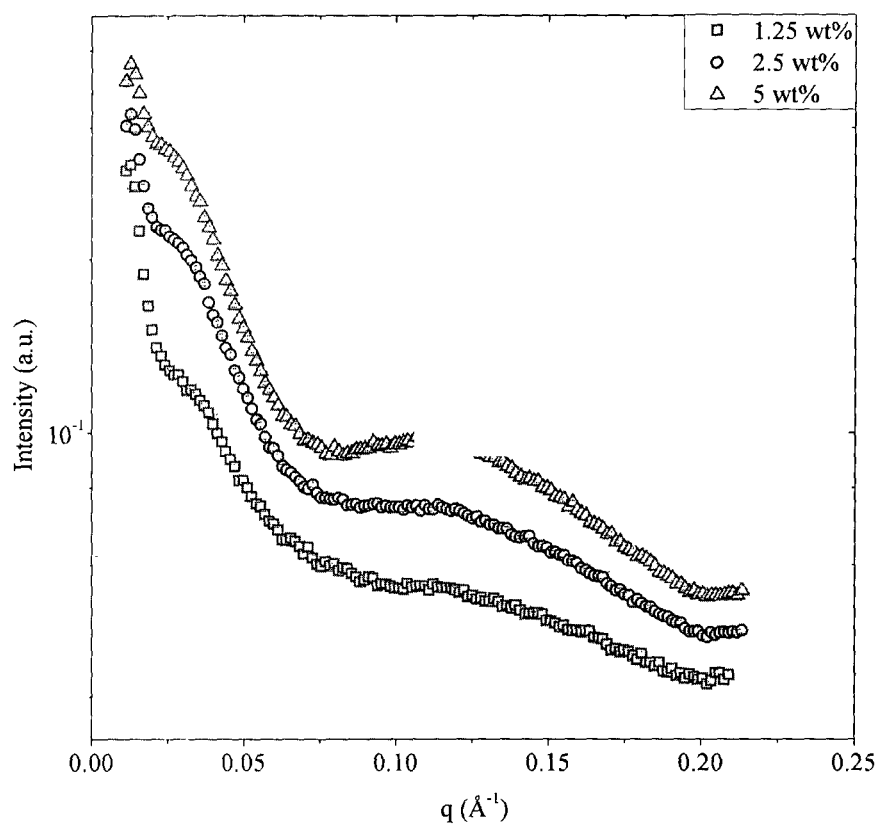
FIG. 4 depicts SAXS from the surfactant-copolymer complex as a function of concentration.

SAXS study of the $C_{12}E_9$-PMAVME complex as a function of concentration indicates a low q peak (that we interpreted as the correlation peak for the PMAVME copolymer polyelectrolyte) and a high q peak (that arrives from the correlation between the surfactant micelles associated with the PMAVME copolymer) as depicted in FIG. 4.

Figure 5:
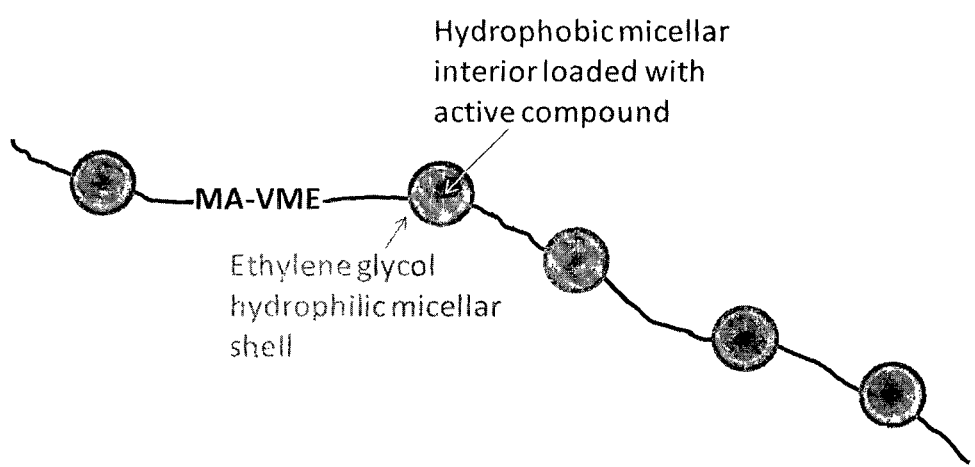
FIG. 5 depicts schematic representation of the structure of surfactant-copolymer complex, with surfactant micelles loaded with hydrophobic compounds decorating the copolymer chain.

The structure determination study revealed that the $C_{12}E_9$-PMAVME (i.e. nonionic surfactant-copolymer) complexes exhibits to be pearls on a string, wherein the pearls are the $C_{12}E_9$ non-ionic surfactant micelles loaded with the active/antibacterial material of interest and the PMAVME copolymer is the string that threads these surfactant micelles and specifically anchors micelles loaded with active/antibacterial materials to the area of application. A schematic representation for the structure of the $C_{12}E_9$-PMAVME (i.e. nonionic surfactant-copolymer) complex at low concentrations is depicted in FIG. 5.

Release Profile of Hydrophobic Compounds

The hydrophobic compounds in the $C_{12}E_9$-PMAVME (i.e. nonionic surfactant-copolymer) complexes have an initial rapid release followed by sustained release. Experiments were set up using pyrene as a model for the hydrophobic compound. This was done from a layer of the $C_{12}E_9$-PMAVME complex, containing pyrene within the $C_{12}E_9$ micelles, adsorbed onto a polyethyleneimine (PEI) covered quartz slide.

Figure 6:
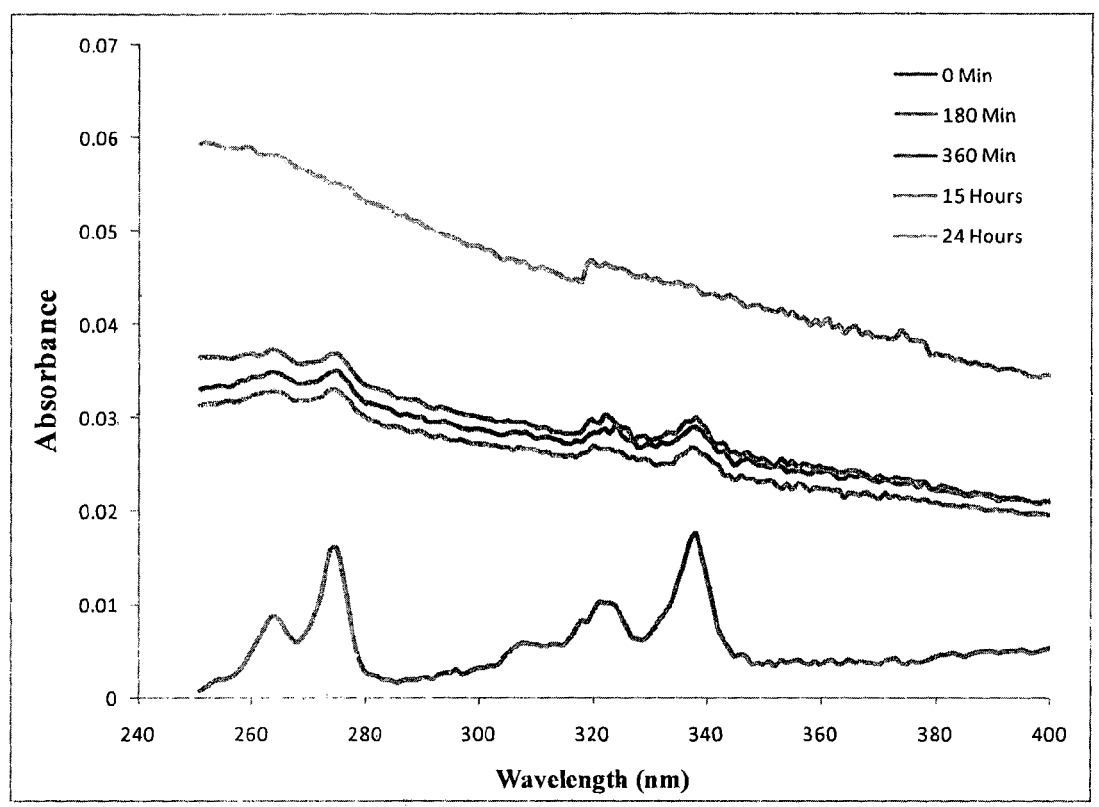
FIG. 6 depicts UV-Visible data from a quartz slide containing an adsorbed layer of PEI and a layer of the complex containing pyrene dye. The data represent the UV-Visible as a function of time when the slide is dipped in water.

The FIG. 6 exhibits UV-Visible data from a quartz slide containing one layer of polyethyleneimine (PEI) and one layer of the $C_{12}E_9$-PMAVME (i.e. nonionic surfactant-copolymer) complex containing the pyrene dye. The bottom curve (blue) exhibits the absorption of the slide after washing with water, immediately after adsorbing the complex. The characteristic peaks of the pyrene absorption are clearly visible indicating that (i) pyrene was "stored" in the hydrophobic region of the $C_{12}E_9$-PMAVME complex and (ii) that the $C_{12}E_9$-PMAVME complexes are adsorbed onto the slide. Further, the slide is left dipped in water for a period of time, and is periodically removed for UV-Visible measurements. It was observed that after being immersed in water for 180 min (3 hours), the extent of the UV-visible signal was decreased; which indicated a sudden release of the pyrene in the first three hours. However, there was no significant decrease in the pyrene UV-Visible peaks between 3 hours and 15 hours, suggesting that at least some of the pyrene does not release from the adsorbed complex even on storing the adsorbed complex in water for up to 15 hours. On immersing in water for 24 hours, it is observed that the pyrene UV-visible peaks disappeared, indicating complete release of the hydrophobic dye over a period of a day.

Figure 7:
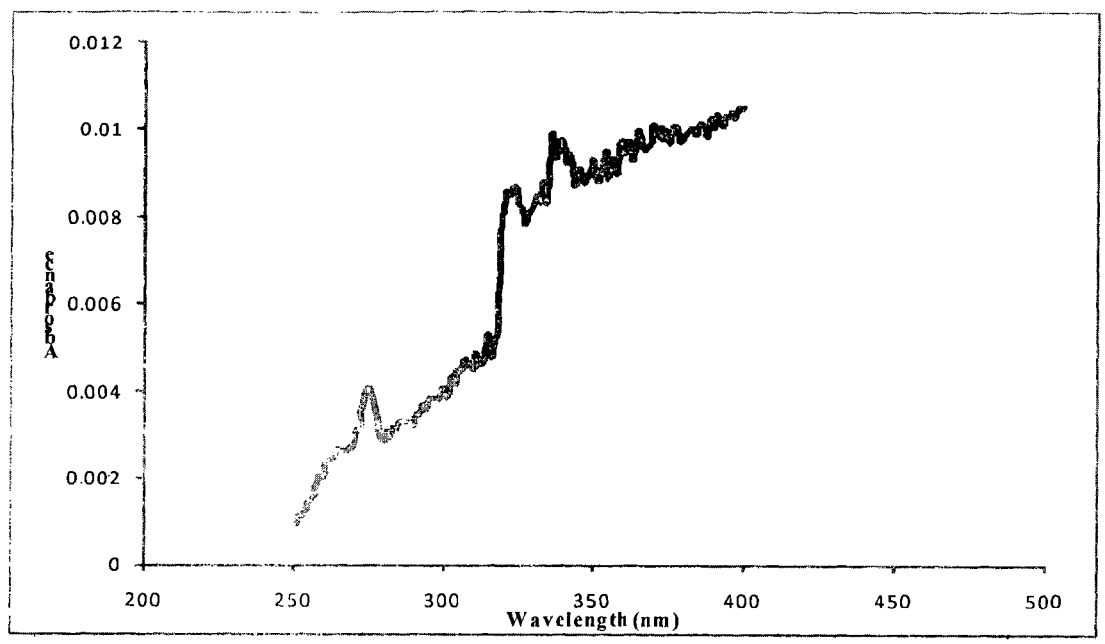
FIG. 7 depicts UV-Visible data from a quartz slide containing an adsorbed layer of PEI and, a layer of the surfactant-copolymer complex containing pyrene dye. Adsorption of the surfactant-complex containing dye was performed from a 10% SDS solution.

Study on Activity of $C_{12}E_9$-PMAVME Complex in Both Aqueous and Anionic Surfactant The $C_{12}E_9$-PMAVME (i.e. nonionic surfactant-copolymer) complexes remain intact and retain their function both in aqueous and anionic surfactant solutions. TO validate the fact, the $C_{12}E_9$-PMAVME complex containing pyrene was adsorbed onto a glass slide covered with polyethyleneimine (PEI), even from a 10% Sodium dodecyl sulphonate (SDS) solution as depicted in FIG. 7. This indicates the stability of the $C_{12}E_9$-PMAVME complex, and its ability to retain the pyrene dye even in the presence of the anionic surfactant.

EXAMPLES

The following examples are given by way of illustration and therefore should not be construed to limit the scope of the present invention.

Example 1

Preparation of Tween 40-PMAVME (Surfactant-Copolymer) Complex Loaded with Hydrophobic Compound A 7% solution of PMAVME was prepared by slowly adding, and continuously stirring PMAVME powder into distilled deionized water over a period of an hour (7 g of PMAVME powder in 93 g of water). Stirring was continued over a day to dissolve the PMAVME, which formed a turbid solution. Separately, menthol (1 g) was dissolved into 5 g of Tween 40 (neat liquid) at room temperature (30° C.). The menthol/Tween 40 mixture was then added to 94 g of water so as to produce a micellar solution of Tween 40, into which the menthol was encapsulated. The PMAVME-Tween 40 complex was prepared by mixing equal weights of the PMAVME solution and the menthol-loaded micellar Tween 40 solution.

Preparation of $C_{12}E_9$-PMAVME (Surfactant-Copolymer) Complex

A non-ionic surfactant, $C_{12}E_9$ obtained from Aldrich and poly (maleic acid-alt-vinyl methyl ether), a commercial alternating copolymer called Gantrez (manufactured by ISP). Further, the $C_{12}E_9$ is a nonionic surfactant comprising of a $C_{12}$ hydrophobic chain and a non ethyleneglycol hydrophilic unit.

The poly (maleic acid-alt vinyl methyl ether) copolymer powder [i.e. PMAVME copolymer] (7 g) was readily dispersed in distilled deionized water (93 g) over a period of an hour and the resultant solution was stirred over a day to dissolve the PMAVME copolymer; and a milky turbid solution of PMAVME copolymer was obtained. Further, $C_{12}E_9$ nonionic surfactant (5 g) was added to the obtained milky solution of PMAVME copolymer in 1:1 molar ratio to obtain a clear solution of $C_{12}E_9$-PMAVME complex.

Evidence for Hydrophobic Loading, for Extended Release of the Hydrophobic Compound from the $C_{12}E_9$-PMAVME (i.e. Surfactant-Copolymer) Complex $C_{12}E_9$-PMAVME complexes were prepared containing a hydrophobic dye, pyrene and such complex was subsequently deposited using layer-by-layer techniques on a glass slide.

The protocol for layer-by-layer technique is as follows:
1. The glass slide was etched using a piranha solution to clean the slide and generate a negative charge on the surface.
2. This slide was dipped in an aqueous solution of polyethyleneimine (PEI) (25000 g/mol) containing 10 mM NaCl salt. The polyethyleneimine (PEI) adsorbed strongly on the surface of the slide.
3. Subsequently, the slide was washed in distilled deionized water to remove the loosely bound polyethyleneimine (PEI).
4. Finally, the slide was dipped in (a) an aqueous solution of the $C_{12}E_9$-PMAVME complex containing a hydrophobic compound, pyrene, or (b) in an aqueous 10% SDS (Na-dodecyl sulphonate, a common anionic surfactant) solution of the complex containing pyrene. Finally, these slides were washed with distilled deionized water and dried. Pyrene was used as a model hydrophobic compound and the release profile of pyrene was determined.

Example 3

Preparation of Tween 40-PMAVME (Surfactant-Copolymer) Complex Loaded with Hydrophobic Compound A 25.4% solution of PMAVME was prepared by slowly adding and continuously stirring PMAVME powder into a mixture of 2 parts of distilled deionized water and 1 part of glycerine over a period of an hour (14 g of PMAVME powder in 30 g of water and 15 g of IP grade glycerine). The PMAVME formed a turbid solution by stirring for over 8 hours. Separately, menthol (3 g) was dissolved into 15 g of Tween 40 (neat liquid) at room temperature (27° C.). The menthol/Tween 40 mixture was then added to 26 g of water so as to produce a micellar solution of Tween 40, into which the menthol was encapsulated. The PMAVME-Tween 40 complex was prepared by mixing the PMAVME solution (59 g) and the menthol-loaded micellar Tween 40 solution (44 g).

Example 4

Preparation of Tween 40-PMAVME (Surfactant-Copolymer) Complex Loaded with Hydrophobic Compound A 25.4% solution of PMAVME was prepared, by slowly adding and continuously stirring PMAVME powder into a mixture of 2 parts of distilled deionized water and 1 part of ethanol over a period of an hour (14 g of PMAVME powder in 30 g of water and 15 g of ethanol). The PMAVME formed a turbid solution by stirring for over 8 hours. Separately, menthol (3 g) was dissolved into 15 g. of Tween 40 (neat liquid) at room temperature (between 25° C. to 30° C.). The menthol/Tween 40 mixture was then added to 26 g of water so as to produce a micellar solution of Tween 40, into which the menthol was encapsulated. The PMAVME-loaded micellar Tween 40 solution (44 g).

ADVANTAGES OF PRESENT INVENTION

The hydrophobic compound delivery is initially rapid, then sustained, thus having better and long term effects in areas of application such as oral health care; perfumes etc.

Amount of the loaded hydrophobic compound in surfactant-copolymer complex (i.e. nonionic surfactant-copolymer complex) and subsequently the cost of making the end product are reduced.

The surfactant-copolymer complex localizes in the area of application, hence action is not diffused.

The surfactant-copolymer complex (i.e. nonionic surfactant-copolymer complex) retains the structure and functions both in aqueous and anionic surfactant.

The surfactant-copolymer complex has wide applications in delivery devices for various hydrophobic compounds such as antibacterials, ointments, drugs/bioactives, perfumes, flavors, pesticides etc.

The invention claimed is:

1. A hydrophobic compound loaded surfactant-copolymer complex for sustained and controlled release of hydrophobic compounds, the surfactant-copolymer complex comprising a hydrophobic compound in the range of 0.1% to 10% (by weight), a surfactant in the range of 0.1% to 30% (by weight) and a mucoadhesive copolymer in the range of 0.1% to 30% (by weight) and the remaining being a solvent, wherein the complex is constituted to perform the sustained release of the hydrophobic compounds over a period of 13-23 hours, prepared by a process comprising the steps of:
   a) dispersing mucoadhesive copolymer in solvent in a ratio ranging between 1% to 40% to obtain turbid solution of mucoadhesive copolymer;
   b) dissolving the hydrophobic compound in surfactant in a ratio ranging between 1% to 50% (weight of hydrophobic compound by weight of the surfactant) at temperature in the range of 10° C. to 80° C. to obtain hydrophobic compound-surfactant mixture;
   c) adding hydrophobic compound-surfactant mixture as obtained in step (b) in water to obtain surfactant solution loaded with hydrophobic compound;
   d) adding surfactant solution loaded with hydrophobic compound as obtained in step (c) to the turbid solution of mucoadhesive copolymer as obtained in step (a) to obtain hydrophobic compound loaded surfactant-copolymer complex.

2. The hydrophobic compound loaded surfactant-copolymer complex as claimed in claim 1, wherein said hydrophobic compound is selected from the group consisting of antibacterials, drugs, bioactives, perfumes, flavors, pesticides or combination thereof.

3. The hydrophobic compound loaded surfactant-copolymer complex as claimed in claim 1, wherein said surfactant is a nonionic surfactant.

4. The hydrophobic compound loaded surfactant-copolymer complex as claimed in claim 1, wherein said nonionic surfactant is selected from the group consisting of nonaoxyethylene-n-dodecyl ether ($C12E_9$), polysorbate 20 (Tween 20), polysorbate 40 (Tween 40), polysorbate 60 (Tween 60), polysorbate 80 (Tween 80) or combination thereof.

5. The hydrophobic compound loaded surfactant-copolymer complex as claimed in claim 1, wherein said mucoadhesive copolymer used is poly (maleic acid-alt-vinyl methyl ether).

6. The hydrophobic compound loaded surfactant-copolymer complex as claimed in claim 5, wherein said mucoadhesive copolymer poly (maleic acid-alt vinyl methyl ether) is a copolymer of methyl vinyl ether and maleic acid or anhydride, alkali or alkaline salt, C1 to C6 alkyl ester, or free acid thereof.

7. The hydrophobic compound loaded surfactant-copolymer complex as claimed in claim 1, wherein the weight ratio of surfactant to copolymer is 1:1.

8. The hydrophobic compound loaded surfactant-copolymer complex as claimed in claim 1, wherein hydrophobic compound is in the range of 1 to 50% by weight of the surfactant-copolymer complex.

9. The hydrophobic compound loaded surfactant-copolymer complex as claimed in claim 1, wherein said solvent is selected from the group consisting of distilled deionized water, glycerine, ethanol or combination thereof.

10. A hydrophobic compound loaded surfactant-copolymer complex for sustained release of hydrophobic compounds, the surfactant-copolymer complex comprising a hydrophobic compound in the range of 0.1% to 10% (by weight), a surfactant in the range of 0.1% to 30% (by weight) and a mucoadhesive copolymer in the range of 0.1% to 30% (by weight) and the remaining being a solvent, wherein the complex is constituted to perform the sustained release of the hydrophobic compounds over a period of 13-23 hours, wherein said surfactant is selected from the group consisting of nonaoxyethylene-n-dodecyl ether ($C_{12}E_9$), polysorbate 20 (Tween 20), polysorbate 40 (Tween 40), polysorbate 60 (Tween 60), polysorbate 80 (Tween 80) or a combination thereof, and wherein the weight ratio of said surfactant to said copolymer is 1:1.

* * * * *